(12) United States Patent
Gong et al.

(10) Patent No.: US 9,612,164 B2
(45) Date of Patent: Apr. 4, 2017

(54) LOW-PROFILE WIRELESS PASSIVE RESONATORS FOR SENSING

(71) Applicant: University of Central Florida Research Foundation, Inc., Orlando, FL (US)

(72) Inventors: Xun Gong, Oviedo, FL (US); Linan An, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 245 days.

(21) Appl. No.: 14/338,489

(22) Filed: Jul. 23, 2014

(65) Prior Publication Data

US 2015/0028889 A1 Jan. 29, 2015

Related U.S. Application Data

(60) Provisional application No. 61/857,884, filed on Jul. 24, 2013.

(51) Int. Cl.
*G01K 7/24* (2006.01)
*G01N 22/02* (2006.01)
*G01K 11/26* (2006.01)

(52) U.S. Cl.
CPC ............. *G01K 7/24* (2013.01); *G01K 11/26* (2013.01); *G01N 22/02* (2013.01)

(58) Field of Classification Search
CPC .......... G01K 7/24; G01K 11/26; G01N 27/04; G01N 22/02; G01N 27/046
See application file for complete search history.

(56) References Cited

U.S. PATENT DOCUMENTS

| 8,558,705 | B2 | 10/2013 | Gong et al. | |
| 9,214,730 | B2 | 12/2015 | Ley | |
| 2010/0321191 | A1* | 12/2010 | Gong | G01N 22/02 340/584 |

* cited by examiner

*Primary Examiner* — Son Le
*Assistant Examiner* — Brent J Andrews
(74) *Attorney, Agent, or Firm* — Jetter & Associates, P.A.

(57) ABSTRACT

A resonator for sensing a physical or an environmental parameter includes a support having a top surface that provides a ground plane, and a polymer-derived ceramic (PDC) element positioned on the top surface including a PDC layer, and a metal patch on the PDC layer. The metal patch is electrically isolated from all surrounding structure, and the resonator has a resonant frequency that changes as a function of the physical or environmental parameter. A system for wirelessly sensing a physical or environmental parameter includes at least one resonator and a wireless RF reader located remotely from the resonator for transmitting a wide-band RF interrogation signal that excites the resonator. The wireless RF reader detects a sensing signal retransmitted by the resonator and includes a processor for determining the physical or environmental parameter at the location of the resonator from the sensing signal.

18 Claims, 5 Drawing Sheets

LOW-PROFILE WIRELESS PASSIVE RESONATORS FOR SENSING

CROSS REFERENCE TO RELATED APPLICATIONS

This application claims the benefit of Provisional Application Ser. No. 61/857,884 entitled "LOW-PROFILE WIRELESS PASSIVE RESONATORS FOR SENSING", filed on Jul. 24, 2013, which is herein incorporated by reference in its entirety.

STATEMENT REGARDING FEDERALLY SPONSORED RESEARCH

This invention was made with U.S. Government support under National Science Foundation (NSF) contract ECCS-0823950 and under Department of Energy (DOE) contract DE-FE0001241. The U.S. Government has certain rights in this invention.

FIELD

Disclosed embodiments are related to wireless passive resonators for sensing and wireless sensing systems therefrom.

BACKGROUND

Turbine engines currently play a dominant role in systems including power generation and aircraft propulsion. Current turbine designs have been limited by the lack of sensors capable of reliably providing detailed physical and chemical data in high-temperature (e.g., >1,000° C.) sections of such systems. For example, to further improve the performance and reliability and to reduce the pollution of turbine engines, robust sensors and sensor networks are needed for next-generation turbine technology to enable (i) obtaining detailed thermo-mechanical data to refine engine designs, (ii) providing online, real-time monitoring, and (iii) providing intelligent controls to make the engines "smart".

Currently, several technologies are under development for measuring the physical and chemical parameters within turbine engines. Optical-based non-contact technology is known for determining these parameters. However, optical-based non-contact technology has been shown to lack the necessary measurement accuracy and typically breaks down over time. Another technique measures these parameters without disturbing the work environment comprises using miniature sensors. Silicon carbide (SiC) and silicon nitride ($Si_3N_4$)-based ceramic microsensors have been investigated for high temperature and harsh environment applications. However, these sensors are restricted by limited fabrication methods, high cost, and a limited operation temperature range (typically <800° C.).

Polymer-derived ceramic (PDC)-based sensors and sensing systems using such materials are also known. PDC materials are generally formed by the processing of materials referred to as "preceramic polymers". Preceramic polymers are conventionally defined as polymers whose backbone contains C and at least one eteroatom (usually Si) that provides a ceramic residue (the PDC) through the elimination of organic moieties by breaking of C—H bonds, and release of $H_2$ and $CH_4$ and other volatile compounds. The term "eteroatom" is used to indicate any atom of a cyclic molecule or of a cyclic portion of a molecule or ion that is not carbon. The polymer-to-ceramic conversion is achieved either thermally (pyrolysis) or non-thermally (for instance by irradiation with ions), usually processing in controlled atmosphere. Polysiloxanes, polycarbosilanes, polysilanes and polysilazanes are some of the preceramic polymers currently available commercially, and they allow production of $SiO_2$, SiOC, SiC, $Si_3N_4$ and SiCN ceramics.

In one disclosed system for measuring the temperature or strain in an aircraft, PDC-based sensors are wired to a signal processing system. This system senses a resistance change due to the temperature/strain change experienced by the sensors. A limitation of the wired sensing arrangement is that it cannot be used for measurements in difficult to reach locations, such as important sections in turbine engines such as the turbine blades, and sections that are blocked by the turbine blades. There is thus a need for new high temperature (e.g., >1,000° C.) capable sensors and sensing systems that can sense parameters in any section of a turbine engine, or in other space-limited high-temperature and harsh environment applications.

SUMMARY

This Summary is provided to introduce a brief selection of disclosed concepts in a simplified form that are further described below in the Detailed Description including the drawings provided. This Summary is not intended to limit the claimed subject matter's scope.

Disclosed embodiments include wireless, passive resonators for sensing and sensing systems therefrom based on polymer-derived ceramic (PDC) sensing elements which include a metal patch on a PDC layer. The PDC element functions as a reflective patch. Disclosed embodiments recognize PDCs are high temperature tolerant (>1,000° C.), low loss tangent, and also provide a temperature-dependent dielectric constant. Accordingly, for temperature sensing applications, the resonant frequency of the PDC element changes as a function of the temperature allowing the resonator to provide a signal indicative of its temperature.

The metal patch on the PDC layer does not have any transmission line connected to it as a standard patch antenna would. Therefore, disclosed PDC elements are quite distinct from a patch antenna, and are instead configured together with a ground plane to provide a patch resonator. Normally a patch resonator structure would not be a good antenna, meaning the resonator cannot transmit (or receive) energy into the free space with a reasonable efficiency. Therefore one having ordinary skill in the art would expect not being able to sense the resonant frequency of the patch resonator.

However, it was unexpectedly discovered that there is a critical condition and associated condition range under which the unloaded quality (Q) factor of the resonator is at least substantially equal to the radiation Q factor of the resonator. The Q factor for a resonator is a dimensionless quantity generally defined in terms of the ratio of the energy stored in the resonator to the energy dissipated per cycle. If only the losses inside of the resonator, such as dielectric losses and metallic losses, are considered, this Q factor is referred to herein as an "unloaded Q", while if only the loss due to the radiation from the resonator is considered, then the Q factor is referred to herein as the "radiation Q".

If this "Q-factor matching" condition is met for the resonator, it has been discovered energy can be efficiently transmitted to/from the patch of the resonator. In this sense, the patch (together with the PDC and a ground plane) acts as a resonator (sensor) and an antenna at the same time. This is believed to be the first time a high-Q patch-based resonator has been used for such dual purposes. In addition, this structure and theory behind it provides a new design of high-temperature tolerant sensors having robustness and low profile.

Disclosed PDC elements thus provide both the sensor and the antenna for wirelessly sensing at least one physical or environmental parameter. The ground plane under the PDC element completes the resonator. If the supporting material under the PDC element does not provide a ground plane, a ground plane can be provided for the resonator. If the supporting material is a metal (e.g., a conventional turbine blade), the metallic supporting material can be used the ground plane. An advantage of disclosed resonators is that if the supporting material is metal, the resonator will still properly operate as a sensor. Many other sensor structures will not work on a metallic supporting material.

Disclosed embodiments recognize PDCs are readily patternable using conventional lithography in their precursor state, so that disclosed PDC elements can be created by patterning a metal layer on top of a patterned PDC layer, resulting in a planar resonator. Disclosed resonators are low profile because there is no need for a transition portion between the PDC sensor portion and the metal patch antenna, which for applications such as for combustion turbines minimizes the adverse effects on aerodynamics inside turbines. Although disclosed embodiments are described using PDCs, other ceramic materials may also be used with disclosed embodiments provided they can be readily patterned, exhibit a temperature-dependent dielectric constant for temperature sensing applications, provide a reasonably low loss tangent (such as <0.02 above 1,000° C.), and can survive harsh environments for applications in harsh environments.

In disclosed sensing systems a wireless RF reader is used in combination with the resonator. Since the wireless RF reader can be spaced apart from the resonator, for high temperature applications the wireless RF reader can be positioned outside the high temperature region and be coupled to an interrogator antenna that is high temperature tolerant which can be positioned proximate to the resonator. The separate wireless reader can send a wide-band modulated signal towards the PDC element functioning as a reflective patch and electromagnetic energy couples into the PDC element, which then reradiates (reflects) electromagnetic energy back to the interrogator antenna for which the reader can detect the resonant frequency by performing signal processing including example time-domain gating and Fourier transform analysis. This disclosed wireless passive approach avoids physical connections to the resonator, which allows for its usage on moving components, such as on rotating components inside turbines (e.g., blades).

BRIEF DESCRIPTION OF THE DRAWINGS

Reference will now be made to the accompanying drawings, which are not necessarily drawn to scale, wherein.

DETAILED DESCRIPTION

Disclosed embodiments in this Disclosure are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments.

One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Figure 1A:
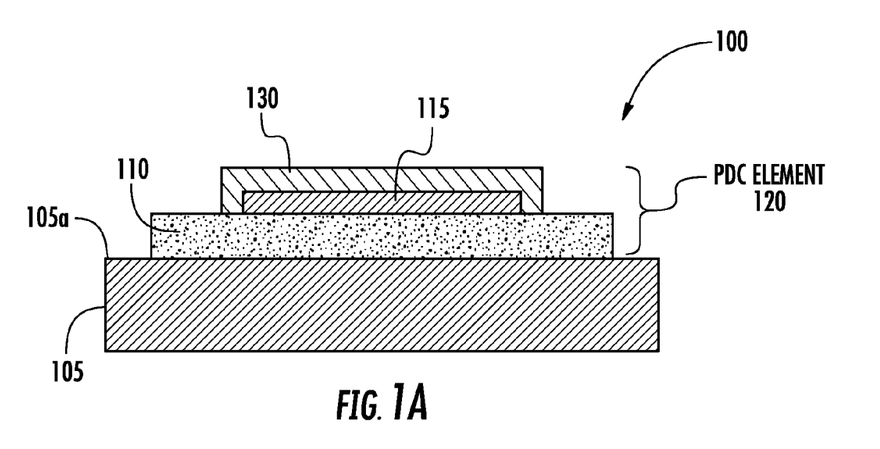
FIG. 1A shows a cross-sectional depiction of an example low profile resonator for sensing temperature, according to an example embodiment.

FIG. 1A shows a cross-sectional depiction of an example low profile resonator 100 for sensing temperature, according to an example embodiment. The resonator 100 includes a support 105 having a top surface 105a that provides a ground plane. A polymer-derived ceramic (PDC) element 120 is positioned on the top surface 105a including a PDC layer 110 and a metal patch 115 on the PDC layer 110. An optional dielectric capping layer 130 is on the metal patch 115 that can optionally encapsulate the metal patch 115 to prevent oxidation of the metal patch 115.

The metal patch 115 is electrically isolated from all surrounding structures, and the resonator 100 has a resonant frequency that changes as a function of the temperature based on the PDC layer's 110 temperature-dependent dielectric constant. Accordingly, the resonant frequency of the resonator 100 changes as the PDC element 120 changes its dielectric constant as a function of the temperature allowing the resonator 100 to signal the temperature, such as to a separate wireless reader which can send a wide-band modulated signal towards the PDC element 120 functioning as a reflective patch which couples electromagnetic energy into the resonator 100, and then reradiates (reflects) electromagnetic energy back to an interrogator antenna coupled to the wireless reader. The wireless reader can detect the resonant frequency by performing signal processing such as time-domain gating and Fourier transform analysis. (See the block diagram of an example wireless sensor system described below relative to FIG. 4A).

The Inventors have also recognized that PDCs have excellent microfabrication capability and compatibility with existing silicon-based microfabrication (e.g., MEMS) processing. Unlike conventional ceramic materials (e.g., SiC and $Si_3N_4$), PDC-based micro-devices can be fabricated using well-developed semiconductor processing technologies, generally including photolithography and deep reactive-ion etching (DRIE) if cavities are needed. PDCs can also be formed by processing organic thin/thick film precursors using spin-on coating methods and patterned into desired thin film or thick film devices. In this process, the precursor for PDCs, which is either a liquid or dissolvable into an organic solvent, can be modified to be photosensitive and processed similar to photoresist and patterned using conventional photolithography.

Significant to disclosed temperature sensing embodiments, the Inventors have recognized that PDCs possess unique temperature-dependent dielectric properties. A property of PDCs such as SiCN is that the electrical conductivity of PDCs can be varied across a large range by tailoring the composition of the materials, from electrical insulator (dielectric) to semiconductor. When in the insulator state, the Inventors have recognized that PDCs possess a dielectric constant that increases monotonically with temperature. This change in dielectric constant, which can be used to monitor temperature according to a disclosed embodiment, is much more significant than that for other high-temperature materials, such as $Al_2O_3$, and thus provides higher measurement sensitivity. Furthermore, the dielectric constant of the PDC element 120 can also be tuned by varying the initial polymer composition to meet different requirements for interfacing with a wireless sensor in a disclosed wireless sensing system.

There is generally no limitation on the shape of the metal patch 115, and rectangular is simply one possible shape, with circular being another example of many other possible shapes. The thickness for the metal patch 115 is typically 1 micron to 10 microns, but is not restricted to this range. The metal patch 115 can comprise a refractory metal that has a melting point >1500° C., such as tungsten (W), tantalum (Ta) platinum (Pt) or titanium (Ti), or related refractory metal compounds such as WN, TaN or TiN.

As noted above, the metal patch 115 on the PDC layer 110 does not have a transmission line connected to it that a conventional patch antenna would require. Therefore, it is not a standard patch antenna, it is rather a patch resonator when combined with a ground plane. Normally this resonator structure would not be a good antenna, which means the resonator would be unable to transmit energy into the free space with a reasonable efficiency. However, it was unexpectedly discovered that there is a critical condition under which the unloaded Q factor of the resonator 100 is substantially equal to the radiation Q factor of the resonator 100 referred to herein Q-factor matching. At this Q-factor matching condition, stated in the equation below, energy can be efficiently transmitted to/from the resonator. In this sense, the resonator acts as a resonator (sensor) and an antenna at the same time. This is believed to be the first time a high-Q patch resonator has been used for such dual purposes. In addition, this structure and theory behind it provides a new design of low-profile high-temperature sensors with robustness and low profile.

As used herein the unloaded Q factor of the resonator 100 being Q-factor matched to the radiation Q factor of the resonator 100 is defined as these quantities being within 50% of one another, or in other embodiments within 30% or within 20%, so that energy can be efficiently transmitted to/from the RF resonator 100. The left side of the equation below is the radiation and surface wave Q factor of the resonator 100 while the right side of the equation below is the unloaded Q factor of the resonator 100.

$$\frac{1}{Q_r} + \frac{1}{Q_s} = \frac{1}{Q_m} + \frac{1}{Q_d}$$

Where Qr, Qs, Qm, Qd are related to radiation loss, surface wave loss, metallic loss, and dielectric loss of the resonator 100, respectively. These Q factors are determined by the size the resonator, dielectric properties of the PDC, and metal properties. Qm and Qd can be approximately calculated using analytic formulas. Qr and Qs can generally only be found using full-wave simulations. All four Q values can be simulated using full-wave solver. RF engineers having ordinary skill in the art can find Q values for a given design based on the aforementioned sensor parameters to allow one to design a resonator that achieves disclosed Q-factor matching. The full-wave simulation software can be the ANSYS High Frequency Structure Simulator (HFSS) provided by ANSYS, Inc.

Figure 1B:
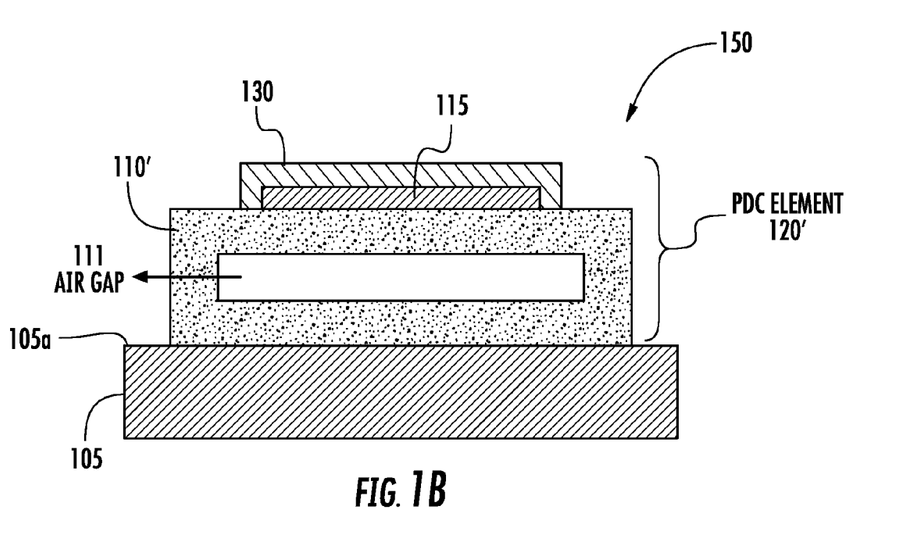
FIG. 1B shows a cross-sectional depiction of an example low profile resonator including an air gap for sensing pressure, according to an example embodiment.

FIG. 1B shows a cross sectional depiction of an example low profile resonator 150 for sensing pressure, according to an example embodiment. The resonator 150 includes a support 105 having a top surface 105a that provides a ground plane. A PDC element 120' is positioned on the top surface 105a including a PDC layer 110' and a metal patch 115 is on the PDC layer 110'. The PDC layer 110' includes an air gap (cavity) 111. An optional dielectric capping layer 130 is on the metal patch 115 that prevents oxidation of the metal patch 115.

As with resonator 100, the metal patch 115 is electrically isolated from all surrounding structures, and the resonator 150 has a resonant frequency that changes as a function of the pressure based on pressure changes changing the distance between the respective plates of the resonator (between the top surface 105a and metal patch 115). Accordingly, the resonant frequency of the resonator 150 changes as a function of the pressure, allowing the resonator 150 to signal the pressure, such as to a separate wireless reader which can send a wide-band modulated signal towards the PDC element functioning as a reflective patch which couples electromagnetic energy into the PDC element, and then reradiates (reflects) electromagnetic energy back to an interrogation antenna coupled to a wireless reader from which the reader can detect the resonant frequency by performing time-domain gating and Fourier transform analysis.

Figures 2A, 2B:
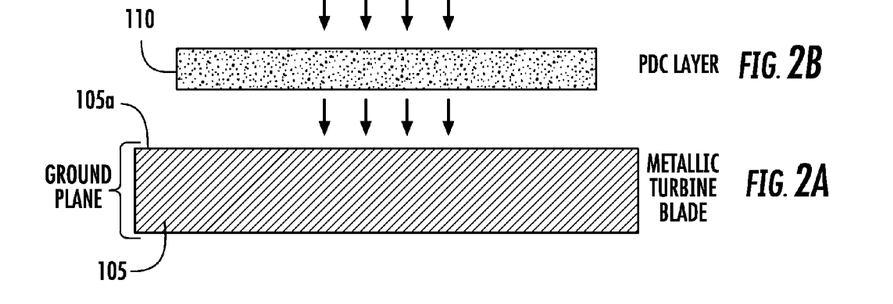
FIGS. 2A-D depicts steps for an example fabrication process for forming the example low profile resonator for sensing temperature shown in FIG. 1A, according to an example embodiment.
Figures 2C, 2D:
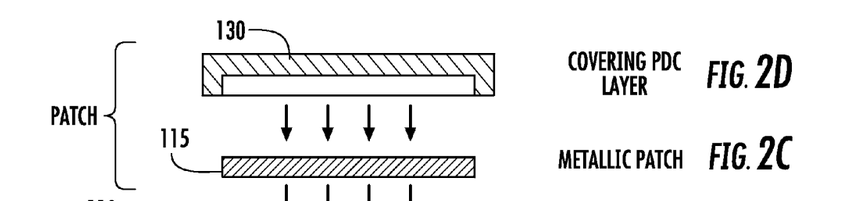

FIGS. 2A-D depict steps of an example fabrication process for forming the example low profile resonator 100 for sensing temperature shown in FIG. 1A, according to an example embodiment. FIG. 2A depicts a metallic turbine blade which provides a support having a top surface 105a that provides a ground plane for the resonator. FIG. 2B depicts a PDC layer 110 on the top surface 105a of the turbine blade after depositing a PDC precursor layer on the top surface, lithographically defining at least one patterned PDC precursor layer, and converting (e.g., by pyrolysis) the patterned PDC precursor layer into the PDC layer 110 shown. FIG. 2C depicts a metal patch 115 after depositing a metal patch on the patterned PDC layer 110 to provide a PDC element. The metal patch 115 is electrically isolated from all surrounding structures, and the resonator due to the temperature dependence of the PDC layer 110 has a resonant frequency that changes as a function of temperature. FIG. 2D shows the optional dielectric capping layer 130 after its deposition on the metal patch 115 which prevents oxidation of the metal patch 115 that completes the low profile resonator 100 shown in FIG. 1A.

Figures 3A, 3B, 3C:
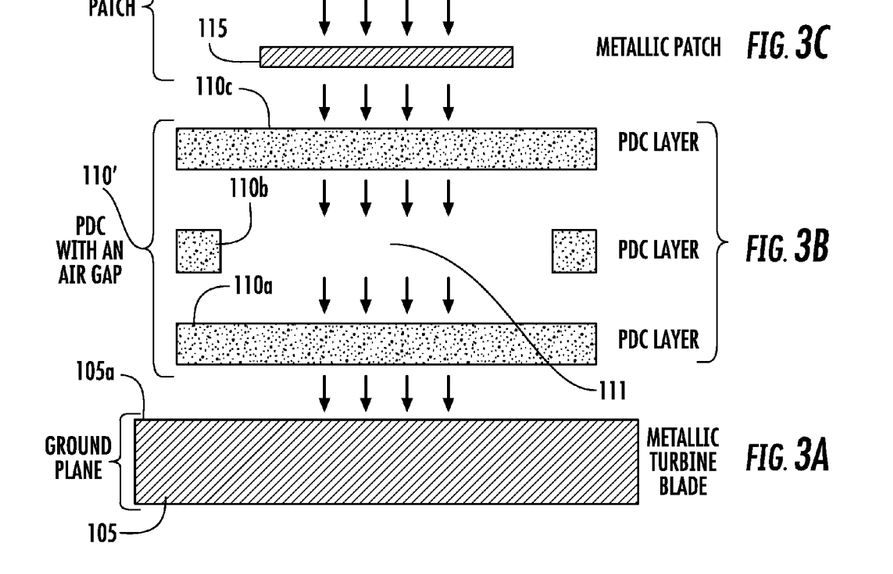
FIGS. 3A-D depicts steps for an example fabrication process for forming the example low profile resonator for sensing pressure shown in FIG. 1B according to an example embodiment.
Figure 3D:
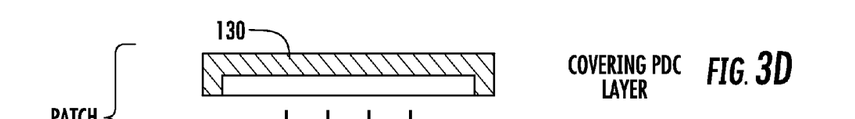

FIGS. 3A-D depict steps for an example fabrication process for forming the example low profile resonator 150 for sensing pressure shown in FIG. 1B according to an example embodiment. FIG. 3A depicts a support 105 shown as a metallic turbine blade (turbine blade support) having a top surface 105a which provides a ground plane for the resonator. FIG. 3B depicts a PDC layer 110' on the top surface 105a of the turbine blade support 105 after depositing a first PDC precursor layer 110a on the top surface, lithographically defining the first PDC precursor layer, depositing a second PDC precursor layer 110b on the first PDL layer 110a, lithographically defining the second PDC precursor layer 110b including forming the air gap 111, depositing a third PDC precursor layer 110c on the second PDL layer 110b, lithographically defining the third PDC precursor layer 110c, and then converting the patterned PDC precursor layers 110a, 110b and 110c into the PDC layer 110' shown in FIG. 1B having the air gap (cavity) 111 shown in both FIG. 1B and FIG. 3B.

The third PDC precursor layer 110c is thin enough to be flexible to function as a membrane that flexes under pressure. For example, an example thickness range for the third PDC precursor 110c layer is 50-200 μm, but disclosed embodiments are not limited to this range. FIG. 3C depicts a metal patch 115 after depositing a metal patch on the patterned PDC layer to provide a PDC element. The metal patch 115 is electrically isolated from all surrounding structure, and the resonator has a resonant frequency that changes as a function of pressure. FIG. 2D shows the optional dielectric capping layer 130 after its deposition on the metal patch 115 which prevents oxidation of the metal patch 115.

The PDC can comprise materials including SiAlCN, SiCN, and SiBCN. PDCs possess complex nano-structures in which nano-crystalline phases (such as SiC or $Si_3N_4$), unique amorphous phases (e.g., SiOC or SiCN) and a free carbon phase (i.e. turbostratic carbon in which C atoms are not directly bonded to Si atoms), co-exist. PDCs are known to provide low creep rate, high chemical resistance and a higher thermal stability in comparison to conventional ceramics such as SiC and $Si_3N_4$. As defined herein, a PDC is a ceramic that includes amorphous phases and a free carbon phase (i.e. turbostratic carbon in which C atoms are not directly bonded to Si atoms), and also includes at least one heteroatom, and resists thermal decomposition and large-scale crystallization up to at least 1,000° C., and generally up to at least 1,200° C. Some PDCs provide resistance to thermal decomposition and large-scale crystallization up to about 1,800° C.

Disclosed resonators and systems are thus high-temperature tolerant (generally at least 1,000° C.) and provide online, real-time monitoring for applications such as in turbine engine systems where survival under extremely harsh conditions (e.g., >1,000° C. and/or a corrosive atmosphere) is needed. Being wireless, such systems also allow sensing in otherwise difficult to reach system locations, including generally any section of a turbine engine, including around the turbine blades. Moreover, the disclosed resonators generally provide Q-factors ≥50 (including at high temperatures, such as >1,000° C.) which enable more accurate and long-range wireless sensing. As used herein, RF is defined as electromagnetic radiation that has a wavelength ranging from hundreds of meters to about one millimeter.

In the system embodiment, a wireless RF reader is located remotely from the resonator, and is generally in a room temperature or a near-room temperature location. The RF reader transmits an RF interrogation signal that is generally a wideband RF signal that includes the resonant frequency of the resonator to excite the resonator, which retransmits a sensing signal in response. As used herein, a "wideband signal" is defined as a signal that covers a frequency spectrum ≥5% fractional bandwidth, where the fractional bandwidth is the ratio of a signal's actual bandwidth to its center frequency. The RF reader detects the sensing signal from the resonator and includes a signal processor for processing the sensing signal to determine the physical or environmental parameter at the location of the sensor, such as temperature or pressure. The RF reader generally includes a non-volatile memory that stores a calibration relation that enables obtaining the parameter of interest from the frequency information contained in the sensing signal. The calibration data can be in table form, such as a relation between temperature/pressure and the resonant frequency.

Disclosed resonators have high-Q factors which enable electromagnetic energy from an interrogation signal received to be stored for a longer time (as compared to lower Q-factor resonators) within the resonator before being retransmitted as a sensing signal back to the wireless reader. The reader therefore is able to receive a stronger sensing signal from the resonator due to the high-Q, and perform signal processing on the stronger signal which enables more accurate and longer-range wireless sensing as compared to known related sensing systems.

Figure 4A:
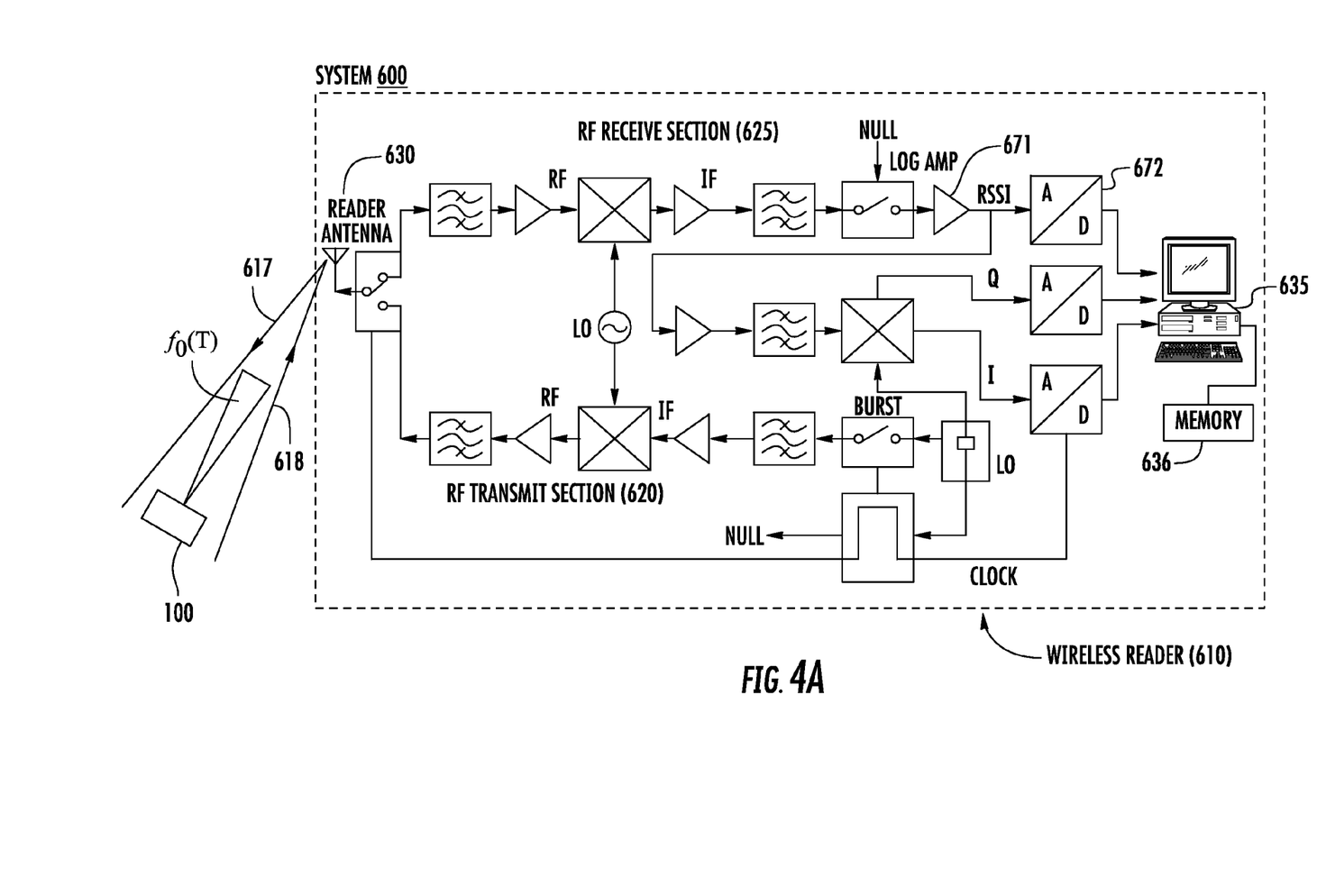
FIG. 4A is a block diagram of a wireless sensor system including a disclosed resonator, according to an example embodiment.

A block diagram of a sensor system 600 comprising a resonator 100 for temperature sensing shown in FIG. 1A and a wireless RF reader (wireless reader) 610 according to an example embodiment is illustrated in FIG. 4A. The resonator 100 for temperature sensing as described above is made of PDCs configured as a resonator by being positioned between metal plates (metal patch 115 and support 105 which can provide a ground plane) which has a resonant frequency $f_o$ that is a function of temperature ($f_o(T)$). Resonator 100 can be miniature (e.g., ~1-10 mm sides) and can be mounted using high temperature tolerant bonding materials to adhere the resonator 100 to the turbine on an engine blade or other high-temperature location (See combustion area 637 shown in FIG. 4C described below), in which resonator resonates at a unique resonant frequency depending on its geometry. The resonant frequency is strongly dependent on patch shape/dimensions and PDC dielectric constant, and weakly dependent on the PDC thickness. The wireless reader 610 includes an RF signal transmit section 620 and RF receive section 625 that is generally located in a room temperature, or near room temperature environment. RF signal transmit section 620 transmits a wide-band RF signal via reader antenna 630 which is received by the resonator 100. The wireless reader 610 detects the sensing signal retransmitted by the resonator 100 which is a function of the temperature or other parameter at the location of the sensor and processor 635 which is coupled to memory 636 that stores signal processing algorithms and calibration data used by processor 635 for processing the sensing signal.

In wireless passive sensing, a time delay between the echoes from the passive transponder and the environment is typically used to isolate the interference from nearby objects and increase sensing accuracy. In conventional SAW sensing systems, delay lines are frequently used for this purpose.

However, long delay lines are very difficult to realize on non-piezoelectric substrates at high temperatures. An alternative is to use a resonator such as resonator 100 which effectively achieves the necessary delay time.

Figure 4B:
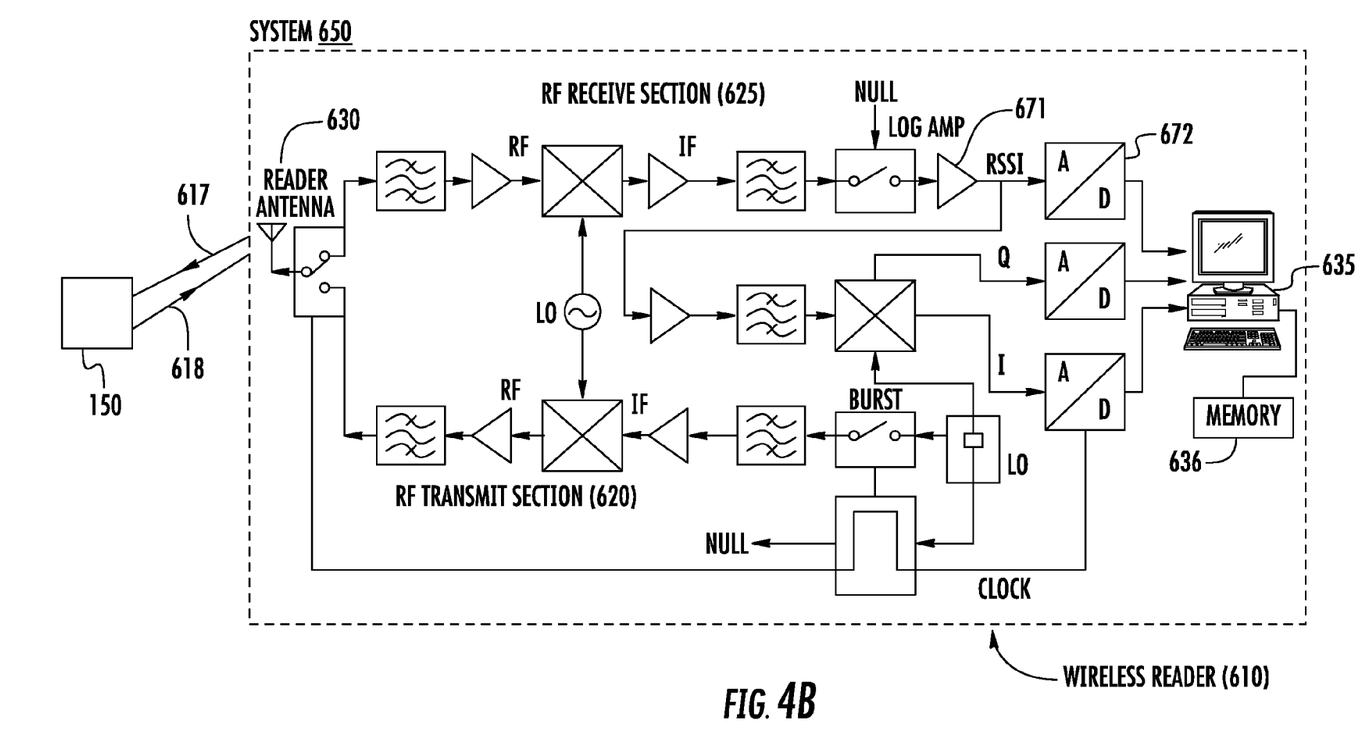
FIG. 4B is a block diagram of a wireless sensor system including a disclosed resonator, according to another example embodiment.

FIG. 4B shows the schematic layout of a sensor system 650 including a resonator 150 for pressure sensing and a wireless reader 610, according to an example embodiment. An interrogation signal 617 shown as a RF request signal from the wireless reader 610 excites the PDC of the resonator 150. The received energy is stored in the PDC of the resonator 150. The number of stored wavelengths is given by the quality factor Q, which also determines the decay time of the resonator 150. This interrogation signal 617 is delayed and retransmitted as the RF response 618 shown by the resonator 100 to the reader antenna 630 of the wireless reader 610.

In order to substantially eliminate the interrogation signal and all environmental echoes (which can contribute noise), the sensing signal response of resonator 150 can be gated in the time domain. After a subsequent Fourier transform, the resulting peaks in the frequency domain can be evaluated by the processor 635 of the wireless reader 610 to retrieve the sensor information. More sophisticated algorithms can be used instead of the Fourier transform to determine the resonant frequency of resonator 150 with higher accuracy.

Figure 4C:
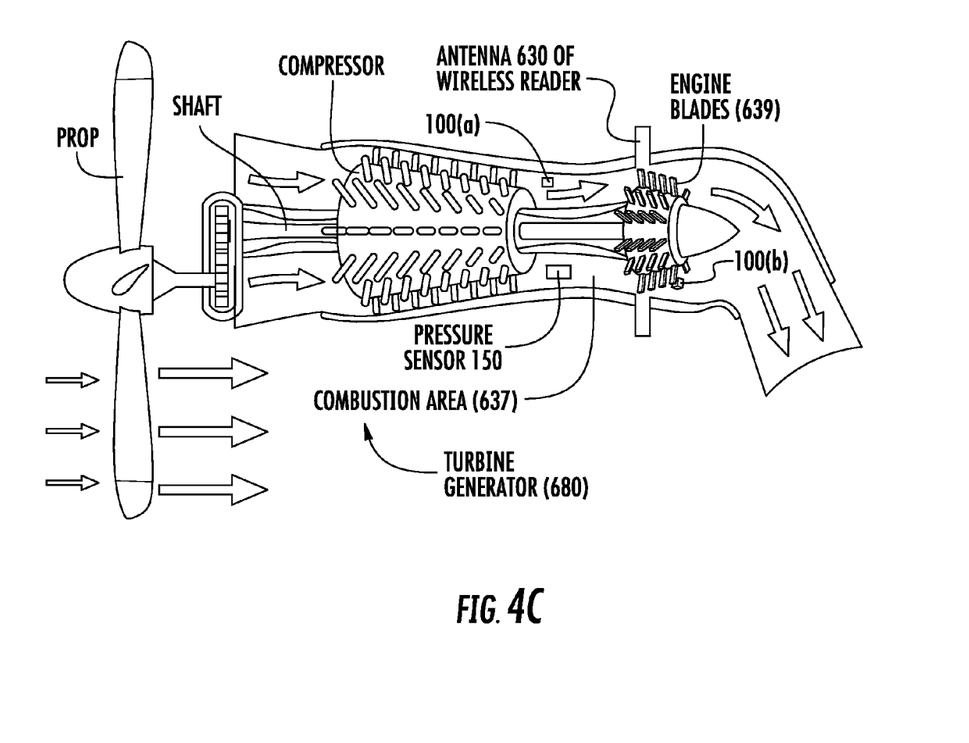
FIG. 4C is a depiction of a system showing a portion of a turbine generator including a plurality of resonators including temperature sensors and a pressure sensor mounted therein, along with a wireless reader, according to an example embodiment.

FIG. 4C is a depiction showing a system section comprising portion of a turbine generator 680 including a plurality of resonators 100 including a resonators 100(*a*) and 100(*b*) for temperature sensing and a resonator 150 for pressure sensing mounted therein within a combustion area 637 using high temperature tolerant bonding materials to adhere the respective resonators. Resonator 100(*b*) is shown on one of the engine blades 639 of the turbine generator 680, along with the antenna 630 of a wireless reader, such as wireless reader 610 in FIGS. 4A and 4B.

The wireless reader for interrogation of the resonators can be similar to those used in conventional radar applications. Particularly, reader unit based on pulsed radars is generally able to achieve best performance values, operation over a broad frequency range, and a high degree of modularity. If there is at least one resonator for temperature sensing within the detection range, it reflects a pulse train after a delay time of several microseconds. The incoming sensor pulses are first amplified then down-converted in the IF-band by the wireless reader 610. The log amplifier 671 following the IF filter (see FIGS. 4A and 4B) has one output for the amplitude and another with the limited signal for detecting the phase information.

A quadrature demodulation as shown can be employed to get the in-phase and quadrature component out of the limited signal. After demodulation and digitizing the A/Ds 672 (see FIGS. 4A and 4B) shown, the sensing signal is evaluated by a processor (e.g. microprocessor) 635 which is coupled to memory 636 (see FIGS. 4A and 4B) for processing the sensing signal. Because the system operates fully coherent with respect to the local oscillator, many RF responses can be summed up to enhance the signal-to-noise ratio (SNR), thus leading to an improvement of the maximum read-out distance.

Although a single resonator for sensing is generally described herein, disclosed such as the turbine generator 680 shown in FIG. 4C can include a plurality of resonators for multiple measurements from multiple locations within the system. Since the resonant frequency of each individual resonator can be tuned to be unique by tailoring its geometry as described above, a single reader unit can be used to detect multiple sensors simultaneously to address the need of temperature/pressure sensing at different sensing locations. Modulation techniques known in the art of communications can also be used to provide an identifier to each resonator in an array of resonators that have the same resonant frequency (e.g., time slots in a time division multiplex).

The fundamental knowledge base and technology disclosed herein can also be used to develop sensors other than for temperature and pressure sensing disclosed above. For example, heat flux sensors, shear sensors, and strain sensors for harsh-environment applications can also be realized.

Example fabrication details will now be described.

Micro-Fabrication and Characterization of High-Temperature Dielectric Properties of PDCs for Resonators for Sensing As described above, it has been demonstrated PDCs can be microfabricated using several known techniques, such as micro-casting and lithography. Lithography-based techniques can be adapted for the fabrication of the resonators. Lithography-based fabrication has many advantages, including excellent patterning capability and dimensional accuracy. However, unlike well-developed photoresist, polymeric precursors that are used to synthesize PDCs generally exhibit poor photo-polymerization capability due to the lack of necessary functional groups, which in turn leads to some processing difficulties.

Processing difficulties include the need for (1) high-energy ultraviolet (UV) source and long exposure times to cure the precursors; and (2) the obtained patterns sometimes lack dimensional accuracy and uniformity. In one embodiment the photo-polymerization ability of the precursors are improved by modifying them with monomers containing vinyl groups. Such vinyl groups, can be added to the precursors through chemical reactions of the precursors and the monomers, and can be easily attacked by free radicals generated by UV exposure of the photo initiator to realize photo-polymerization. Results have indicated that this is an effective approach to improve the patterning capability of PDC thin and thick films.

The dielectric properties of various PDCs were characterized by the Inventors up to 1,200° C. The Inventors have demonstrated that the dielectric constant of PDCs generally increase with increasing temperature up to 1,000° C. and the dielectric constant is expected to increase monotonically up to at least 1,400° C.

Disclosed embodiments provide several significant advantages over conventional sensing systems for sensing pressure or temperature. One advantage is provided by the wireless aspect, specifically being based on a wireless resonant frequency sensing technique. The reader unit, which generally includes a processor having an associated memory with stored calibration data, can read out the temperature/pressure or other parameter information sensed by the passive PDC resonators without the need for wire connections. Therefore, disclosed resonators can be used to measure the temperature/pressure at almost any location inside challenging sensing locations, such as within an engine chamber, including around the rotating engine blades. Resonators having high-Q factor (>3,000 at 20 GHz) have been developed by the Inventor using MEMS. Such resonator structures can also be used for sensing applications. The high-Q factor PDC MEMS resonator structures enable the use of wireless sensing techniques for high-temperature (>1,000° C.) applications.

Another advantage of disclosed embodiments relates to the passive nature of the sensors. Disclosed temperature/pressure sensors do not contain any active device or component since the wireless sensing technique disclosed herein is passive. Only PDC materials and stable metals are used. In addition, as described above, metals can be covered by a high-temperature dielectric coating material to prevent oxidization. As a result, disclosed resonators can be robust even in harsh environments.

High accuracy provided by disclosed embodiments is another advantage. The resonant frequency of the resonator structures disclosed herein has been shown to be very sensitive to the pressure for embodiments having an air gap. Also, the dielectric constant of PDCs has been demonstrated to be strongly temperature-dependent. As described above, wireless sensing techniques based on high-Q factor resonators are able to detect a slight change in the resonant frequency of the resonators, where using stored calibration data the sensed resonant frequency can be converted to a specific temperature or pressure values.

Robustness is another advantage provided by disclosed embodiments. The highly oxidation/corrosion resistant nature of the PDCs makes the sensors robust in extremely harsh environments. Since the RF reader units can be remotely placed in a location that provides a conventional temperature (near room temperature), the potential adverse effects from the high temperature being sensed can be eliminated.

Other advantages provided by disclosed embodiments include small size low profile and flexibility. The size of the passive PDC sensors can be very small depending on the working frequency. Thus, "spot" temperature/pressure sensing becomes possible. Low cost is also generally provided by disclosed embodiments. The cost for fabricating the passive PDC sensors is low due to the small quantities of materials required and the simple and high volume capable processing techniques, such as MEMS. Due to the continued development of RF/microwave circuit technology, the cost of the reader unit is generally modest and will likely continue to decrease in cost.

Disclosed resonators can be widely used in a variety of systems. Example systems include, but are not limited to, high-temperature systems such as turbine engines, turbine generators, nuclear power plants, and rockets, among others.

While various embodiments of the invention have been described above, it should be understood that they have been presented by way of example only, and not limitation. Numerous changes to the disclosed embodiments can be made in accordance with the disclosure herein without departing from the spirit or scope of this Disclosure. Thus, the breadth and scope of this Disclosure should not be limited by any of the above described embodiments. Rather, the scope of this Disclosure should be defined in accordance with the following claims and their equivalents.

The invention claimed is:

1. A resonator for sensing a physical or an environmental parameter, comprising:
   a support having a top surface that provides a ground plane, and
   a polymer-derived ceramic (PDC) element positioned on said top surface including:
      a PDC layer having a top PDC surface and a bottom PDC surface, said bottom PDC surface on said top surface, and
      a metal patch on said top PDC surface;
   wherein said metal patch is electrically isolated from all surrounding structures,
   wherein said resonator has a resonant frequency that changes as a function of said physical or said environmental parameter, and
   wherein an unloaded quality (Q) factor of said resonator and a radiation Q factor of said resonator are Q-factor matched being within 50% of one another.

2. The resonator of claim 1, wherein said support is a metal support that provides said top surface.

3. The resonator of claim 1, wherein said support is a non-metal support, further comprising a metal layer between said support and said PDC element.

4. The resonator of claim 1, further comprising a dielectric capping layer on said metal patch that prevents oxidation of said metal patch.

5. The resonator of claim 4, wherein said dielectric capping layer comprises another PDC layer or a layer of $Al_2O_3$.

6. The resonator of claim 1, wherein said PDC layer includes an air gap (cavity) within, and said resonator provides a pressure sensitive resonant frequency that changes as a height of said air gap changes with pressure to provide a pressure sensor.

7. The resonator of claim 1, wherein an unloaded quality (Q) factor of said resonator is $\geq 100$.

8. The resonator of claim 1, wherein a nominal resonant frequency of said resonator is between 1 and 40 GHz.

9. The resonator of claim 1, wherein said PDC element comprises SiAlCN, SiCN or SiBCN.

10. A system for wirelessly sensing at least one physical or environmental parameter, comprising:
    at least one resonator for sensing said physical or said environmental parameter comprising:
       a support having a top surface, and
       a polymer-derived ceramic (PDC) element positioned on said top surface including:
          a PDC layer having a top PDC surface and a bottom PDC surface, said bottom PDC surface on said top surface, and
          a metal patch on said top PDC surface,
    wherein said metal patch is electrically isolated from all surrounding structure, and
    wherein said resonator has a resonant frequency that changes as a function of said physical or said environmental parameter, and wherein an unloaded quality (Q) factor of said resonator and a radiation Q factor of said resonator are Q-factor matched being within 50% of one another, and
    a wireless RF reader located remotely from said resonator, said wireless RF reader for transmitting a wide-band RF interrogation signal that excites said resonator, wherein said wireless RF reader detects a sensing signal retransmitted by said resonator and includes a processor for determining said physical or said environmental parameter at a location of said resonator.

11. The system of claim 10, wherein a nominal resonant frequency of said resonator is between 1 and 40 GHz.

12. The system of claim 10, wherein said support is a metal support that provides said top surface.

13. The system of claim 10, wherein said support is a non-metal support, further comprising a metal layer between said support and said PDC element.

14. The system of claim 10, further comprising a dielectric capping layer on said metal patch that prevents oxidation of said metal patch.

15. The system of claim 10, wherein said PDC layer includes an air gap (cavity) within, and said resonator provides a pressure sensitive resonant frequency that changes as a height of said air gap changes with pressure to provide a pressure sensor.

16. The system of claim 10, wherein said PDC element comprises SiAlCN, SiCN or SiBCN.

17. The system of claim 10, wherein said at least one resonator comprises a plurality of said resonators, said plurality of said resonators bonded to different locations within said system.

18. The system of claim 17, wherein said plurality of said resonators each provide different resonant frequencies.

* * * * *